United States Patent
Hallinen et al.

(10) Patent No.: US 7,252,839 B2
(45) Date of Patent: Aug. 7, 2007

(54) DELIVERY SYSTEM AND A MANUFACTURING PROCESS OF A DELIVERY SYSTEM

(75) Inventors: Esa Hallinen, Lempäälä (FI); Heikki Lyytikäinen, Naantali (FI); Pentti Järvelä, Lahti (FI); Ilkka Kivi, Pirkkala (FI)

(73) Assignee: Schering Oy, Turku (FI)

( * ) Notice: Subject to any disclaimer, the term of this patent is extended or adjusted under 35 U.S.C. 154(b) by 70 days.

(21) Appl. No.: 10/528,237

(22) PCT Filed: Sep. 4, 2003

(86) PCT No.: PCT/FI03/00647

§ 371 (c)(1),
(2), (4) Date: Apr. 14, 2005

(87) PCT Pub. No.: WO2004/026196

PCT Pub. Date: Apr. 1, 2004

(65) Prior Publication Data

US 2006/0016451 A1 Jan. 26, 2006

(30) Foreign Application Priority Data

Sep. 18, 2002 (EP) .................... 02020869

(51) Int. Cl.
- *A61K 9/48* (2006.01)
- *A61K 9/127* (2006.01)
- *B01J 13/02* (2006.01)
- *B01J 13/04* (2006.01)

(52) U.S. Cl. ...................... 424/451; 264/4.1
(58) Field of Classification Search ............ 424/451

See application file for complete search history.

(56) References Cited

U.S. PATENT DOCUMENTS

| | | | | |
|---|---|---|---|---|
| 3,656,483 A | | 4/1972 | Rudel | 128/264 |
| 3,659,596 A | | 5/1972 | Robinson | 128/130 |
| 3,898,986 A | | 8/1975 | Zaffaroni | 128/130 |
| 3,911,911 A | | 10/1975 | Scommegna | 128/130 |
| 4,198,966 A | * | 4/1980 | Kaivola | 128/839 |
| 4,341,728 A | | 7/1982 | Robertson et al. | 264/161 |
| 4,353,363 A | | 10/1982 | Sopena Quesada | 128/130 |
| 4,413,985 A | * | 11/1983 | Wellner et al. | 604/9 |
| 4,578,076 A | * | 3/1986 | Luukkainen et al. | 128/833 |
| 4,724,832 A | * | 2/1988 | Strubel et al. | 128/840 |
| 5,400,804 A | | 3/1995 | Helle et al. | 128/898 |
| 5,494,047 A | | 2/1996 | Van Os | 128/832 |
| 2004/0261799 A1 | * | 12/2004 | Mock | 128/833 |

* cited by examiner

*Primary Examiner*—Thurman K. Page
*Assistant Examiner*—Jennifer Cho
(74) *Attorney, Agent, or Firm*—James C. Lydon

(57) ABSTRACT

A delivery system including a body construction (7) and at least one capsule (8) containing a pharmaceutical composition, the capsule having at least a first end and a second end. The body construction (7, 12, 34) has at least two locking parts (9, 10), each locking part (9, 10) having at least a first end and a second end, the first end of each locking part (9, 10) having a surface adapted to face and cover one of the at least first and second ends of the capsule (8). The diameter of at least one of the locking parts varies along its length between the first end and the second end, and the capsule (8) is mounted between the at least two locking parts. Also disclosed is a manufacturing process of a delivery system, the system including a body construction and at least one capsule containing a pharmaceutical composition.

10 Claims, 7 Drawing Sheets

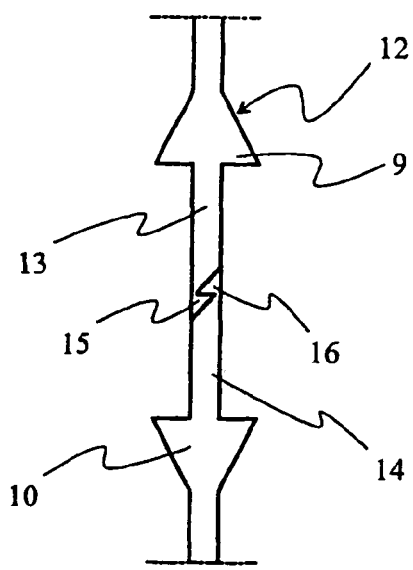
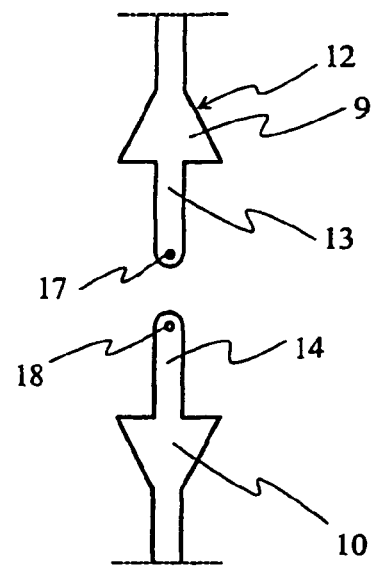
Fig. 4  Fig. 5
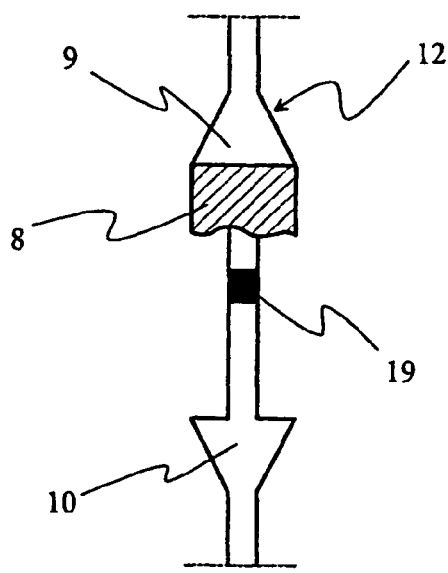
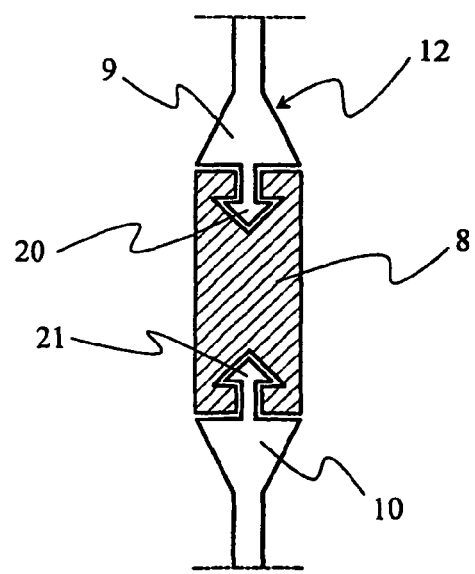
Fig. 6  Fig. 7

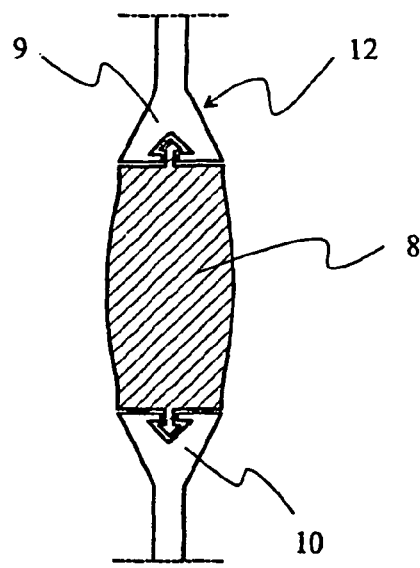
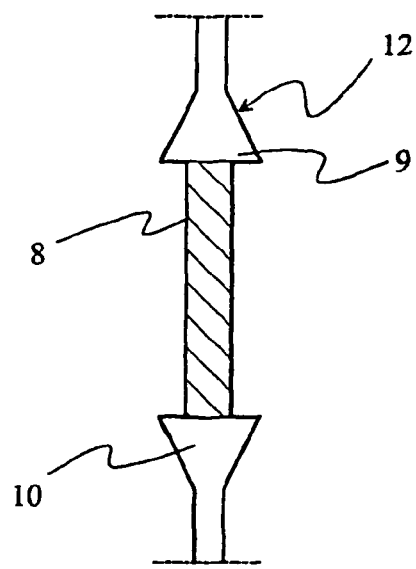
Fig. 8
Fig. 9
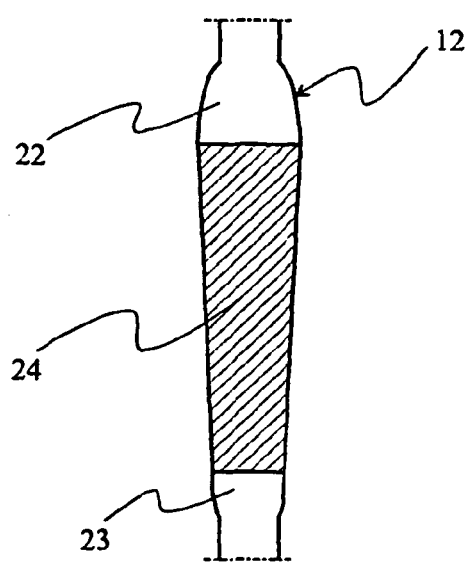
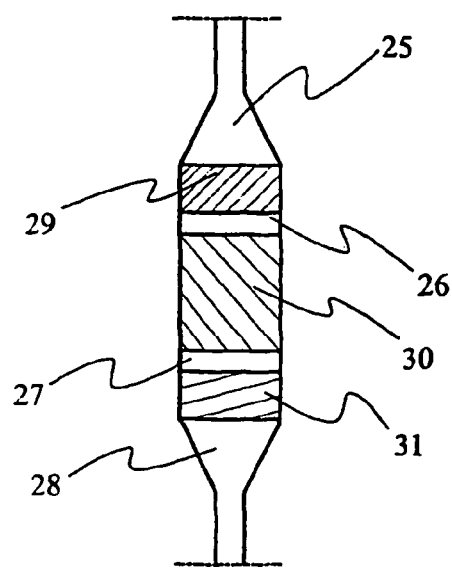
Fig. 10
Fig. 11

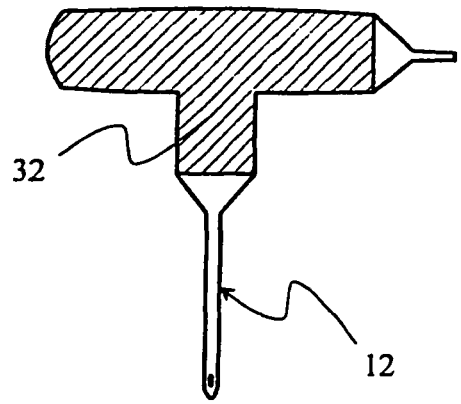
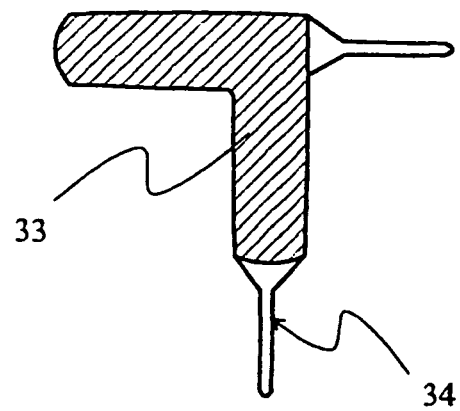
Fig. 12  Fig. 13
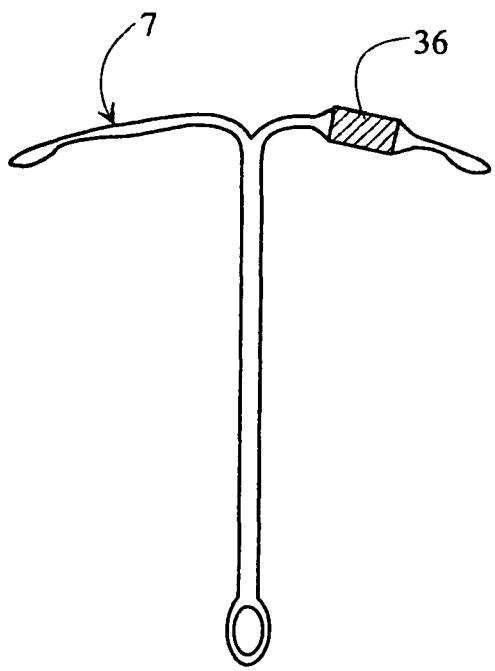
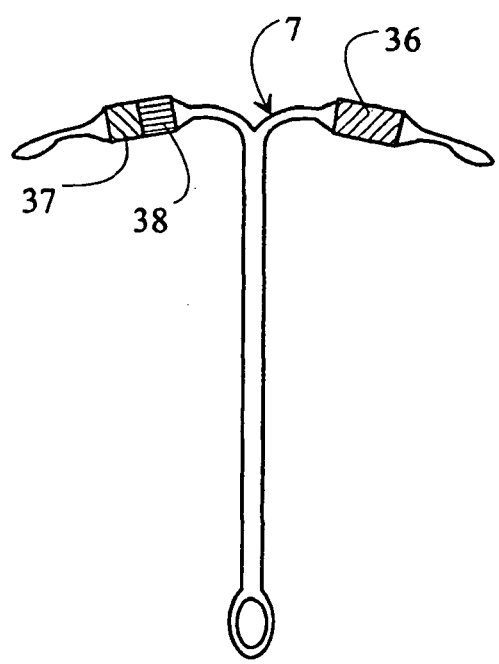
Fig. 14  Fig. 15

DELIVERY SYSTEM AND A MANUFACTURING PROCESS OF A DELIVERY SYSTEM

FIELD OF THE INVENTION

This invention relates to a delivery system comprising a body construction and at least one capsule containing a pharmaceutical composition, said capsule having at least a first end and a second end. This invention further relates to a manufacturing process of a delivery system, said system comprising a body construction and at least one capsule containing a pharmaceutical composition.

BACKGROUND OF THE INVENTION

The publications and other materials used herein to illuminate the background of the invention, and in particular, the cases to provide additional details respecting the practice, are incorporated by reference.

The delivery system discussed in this application mainly covers intrauterine systems (IUS), intracervical systems and intravaginal systems. The systems usually consist of a body and a capsule containing one or more pharmaceutically active agents. A commonly used intrauterine system is a T-shaped object fabricated of plastic material, which object consists of an elongate member having at one end a transverse member comprising two wings, the elongate member and the transverse member forming a substantially T-shaped piece when the system is positioned in the uterus. The elongate member has for example a copper wire wound partly around it, said wire being capable of releasing copper ions (and corresponding to the above-mentioned capsule containing the pharmaceutically active agent). Also IUS's capable of releasing hormones or other active agents exist, and they are used either for contraception or for the treatment of hormonal disorders. In addition to T-shaped IUS's also systems shaped like a ring, a "7" or an "S", for example, are known. Similar constructions are used for the intracervical and intravaginal systems.

The manufacturing process of these systems commonly consists of separate manufacturing of the body and the capsule followed by their assembly. Said assembly is usually performed simply by pulling the capsule over the body, for example over one of the wings. At the beginning of the use of the system, the capsule is tight on the body. However, at the end of the period of use, typically when the capsule has released 30-60% of its content in the active agent, it loosens up and may detach from the body either during the use or at the moment of removal of the system from the body cavity.

The systems are introduced to the appropriate body cavity usually by means of an inserter. Several types of inserters exist for the positioning of intrauterine systems. The most common inserter for T-shaped IUS's consists of a protective tube having a plunger with a handle inside it. In preparation for the positioning of the system in the uterus, the IUS, which is located at the end of the plunger, is retracted towards the handle so that the system enters the tube, and the wings of the transverse member of the system bend towards each other. Then the protecting tube with its contained IUS is introduced through the cervical canal. When the system is correctly positioned it is released by retracting the protecting tube towards the outside. The wings of the transverse member then expand, and the system assumes the shape of a "T".

A problem is associated with the inserters of T-shaped systems and other systems as described above regarding the positioning of the capsule over the body during the retraction of the protective tube towards the outside. The inner diameter of the inserter should be sufficiently larger than the outer diameter of the system to be inserted in order to avoid the shifting or complete detachment of the capsule. However, one has to take into account that the hemispherical end pieces of the wings of the transverse member are small in relation to the diameter of the protective tube. It is, therefore, extremely important that these end pieces are in the exactly correct position in relation to the edge of the protective tube at the moment of introducing the system in the uterus, and therefore the inner diameter of the protective tube cannot be considerably larger than the outer diameter of the system. The difference of the diameters is typically 0.05-0.1 mm. The system is usually sold positioned in the inserter but in the case that the physician unintentionally releases the system too early, it may be very difficult to reposition it correctly in the inserter.

The incorrect positioning of the system in the inserter may cause various problems, such as the shifting of the capsule on the body, the deformation of the capsule, the deterioration of the capsule or the detachment of the capsule.

The shifting of the capsule can for example occur in such a manner that the capsule is displaced towards the wing of the T-shaped system, thus changing the shape to Y and hindering the correct positioning of the wings thus preventing the use of the system. The deterioration or deformation of the capsule may alter the release of the active agent from the capsule.

As discussed above, essentially two problems may occur during the manufacturing of the systems, their introduction into the appropriate body cavity of a patient and their use. These problems are how to assemble the body and the capsule and how to maintain the body and the capsule together during the introduction and the period of use of the system, which may be several years, typically up to five years.

Some solutions to these problems are given in the prior art. For example, the U.S. Pat. No. 4,341,728 discloses a method of making an IUS with shrinking of a medicated attachment onto a support. In said method, a mixture of silicone and a drug is injection moulded to form a sleeve, which is then swollen by immersion in a solvent and subsequently slipped onto a stem of the IUS to shrink about the stem. An outer covering may be positioned over the sleeve in a similar manner. The disadvantage of this method is the use of a solvent. Residues of solvent may remain in the sleeves and cause irritation once the IUS is placed in the patient's uterus. Furthermore, part of the drug may dissolve into the solvent used, thus causing the amount of drug in the final IUS being less than expected. This method does also not solve the problem of maintaining the capsule on the body over the whole period of use of the system.

The U.S. Pat. No. 3,973,560 discloses an IUS consisting of a body and a copper wire, wherein the surface of said body comprises serrations that act as guides for the copper wire and maintain it in place. The disadvantage of this structure is, however, that it is not useful for delivery systems releasing hormones, since these systems do not comprise a wire but rather a tube consisting essentially of an elastomer comprising one or more active agents.

The U.S. Pat. No. 3,656,483 discloses an IUS that consists of a perforated tube containing a supply of medications. The medication is maintained adjacent the perforations by a spring arrangement.

OBJECTS AND SUMMARY OF THE INVENTION

The object of this invention is to provide a delivery system comprising a body construction and at least one capsule containing a pharmaceutical composition, said capsule having at least a first end and a second end, being easy to assemble and ensuring the proper positioning of the capsule on the body during the introduction of the system into the body cavity of the patient, over the period of use of the system and during the removal of the system from the body cavity.

A further object of this invention is to provide an economical and hygienic manufacturing process of a delivery system, said delivery system comprising a body construction and at least one capsule containing a pharmaceutical composition.

DETAILED DESCRIPTION OF THE INVENTION

The invention is disclosed in the appended claims.

The system according to the invention is characterized in that the body construction has at least two locking parts, each locking part having at least a first end and a second end, said first end of each locking part having a surface adapted to face and cover one of the at least first and second ends of the capsule, the diameter of at least one of the locking parts varying along its length between said first end and said second end, and in that the capsule is mounted between said at least two locking parts.

The delivery system according to the invention has thus the following advantages over the prior art systems:
- The system is easier to position in the inserter, since even if the capsule is slightly stuck in the inserter, the capsule cannot shift on the body of the system.
- The capsule is secured between the at least two locking parts so that even if the capsule loosens during the use, it cannot detach from the body of the system.
- The locking parts may be used in the manufacturing process to indicate the optimal position of the capsule on the body of the system.
- The locking parts are advantageously designed to such a shape that once the system is ready for use, there are no sharp discontinuities in the outer surface of the system. Such smooth shape also allows an easier removal of the system from the body cavity.

In the following, some parts of the system are discussed in singular. It is however obvious for a person skilled in the art that the same principles apply even if there are more than one of those parts in the system according to the invention.

The cross-sectional shape and size of the ends of the capsule and the surfaces of the locking parts can be chosen freely. The only restriction is that the surface of the locking part covers the end of the capsule facing it, as disclosed above. The ends of one capsule may have different shapes and sizes and the surfaces of the locking parts may also differ one from another. According to a preferred embodiment of the invention however, the cross-sectional profile of said at least first or second end of the capsule is essentially identical in size and shape to said surface of the locking part facing said end. According to another embodiment of the invention, the cross-section of said at least first or second end of the capsule is essentially smaller than said surface of the locking part facing said end.

According to the invention, it is also possible to freely choose the outer form of the capsule. The capsule may indeed be either symmetrical or asymmetric with respect to any axis of the capsule and it may have any outer form such as for example sinusoidal or conical. The cross-sectional diameter of the capsule may also be constant or variable over the different dimensions of the capsule. According to one of the preferred embodiments of the invention, the outer form of the capsule is such that it allows the formation of a system wherein there are no sharp discontinuities in the outer form, as explained above.

According to yet another preferable embodiment of the invention, said locking parts have the shape of a truncated cone and the end of the truncated cone having a larger diameter is the end having the said surface facing an end of the capsule.

According to an embodiment of the invention, said body construction consists of one body part. According to another embodiment of the invention, said body construction consists of at least two body parts, such as two, three, four or five parts. It is obvious to a person skilled in the art that any number of body parts may be used.

According to a further embodiment of the invention, the system may comprise two or more capsules containing a pharmaceutical composition, typically two, three, four or five capsules. It is again obvious to a person skilled in the art that any number of capsules may be used. Said capsules advantageously contain different pharmaceutically active agents. It is of course also possible to manufacture a system wherein all the capsules contain the same active agent as well as to manufacture a system wherein at least one of the capsules contains several active agents. In such a case, it is possible that all the capsules have different release rates or that the second capsule starts releasing the active agent only once the first capsule's release rate has decreased under a certain threshold value, and so on. Such release profiles are achievables by using appropriate matrixes in the capsules.

According to yet another embodiment of the invention, the capsule containing a pharmaceutical composition consists essentially of a biocompatible polymer and at least one pharmaceutically active agent. The polymer may advantageously be an elastomer. Indeed, when the capsule is made of an elastomer, which is an elastic material, it may easily be pulled over the attachment means during the manufacture of the system. Another advantage of the use of a polymeric material is that it may be injection moulded, thus making the manufacturing process according to this invention easier, as explained below.

The biocompatible polymer used in the capsule may be any suitable polymer known in the art, such as copolymers of ethene and vinyl acetate, polyesters and silicone elastomers and their derivatives as well as any mixtures and blends thereof. The body construction is also manufactured from a suitable polymeric material such as polyethene or polypropene. It is naturally also possible to form the body from another material than polymer, such as metal.

Further examples of suitable materials include polyethylene, polypropylene, polymethylpentene ethylene/propylene copolymers, ethylene/ethyl acrylate copolymers, ethylene/vinyl acetate copolymers, polycarbonate, polytetrafluoroethylene (PTFE), fluoroethylenepropylene (FEP), polyvinylidene fluoride (PVDF), polyvinylacetate, polystyrene, polyamides, polyurethane, polybutadiene, polyisoprene, chlorinated polyethylene, polyvinyl chloride, vinyl chloride copolymers with vinyl acetate, poly(methacrylate), polymethyl(meth)acrylate, poly(vinylidene)chloride, poly(vinylidene)ethylene, poly(vinylidene)propylene, polyethylene terephthalate, ethylene vinylacetate, a polyhydroxy alkoanate poly(lactic acid), poly(glycolic acid), poly (alkyl 2-cyanoacrylates), polyanhydrides, polyorthoesters, ethylene/vinyl alcohol copolymer, ethylene/vinyl acetate/vinyl alcohol terpolymer; ethylene/vinyloxyethanol copolymer, hydrophilic polymers such as the hydrophilic hydrogels of esters of acrylic and methacrylic acids, modified collagen, cross-linked polyvinyl alcohol, cross-linked, partially hydrolyzed polyvinyl acetate, silicone elastomers, especially the medical grade polydimethyl siloxanes, polyvinylmethylsiloxanes, other organopolysiloxanes, polysiloxane, neoprene rubber, butyl rubber, epichlorohydrin rubbers, hydroxyl-terminated organopolysiloxanes of the room temperature vulcanizing type which harden to elastomers at room temperature following the addition of cross-linking agents in the presence of curing catalysts, two-component dimethylpolysiloxane compositions which are platinum catalysed at room temperature or under elevated temperatures and capable of addition cross-linking as well as mixtures thereof.

Especially suitable materials for the capsule and the possible membrane are an elastomer composition comprising poly(dimethylsiloxane), an elastomer composition comprising a siloxane-based elastomer comprising 3,3,3-trifluoropropyl groups attached to the Si-atoms of the siloxane units, an elastomer composition comprising poly(alkylene oxide) groups, said poly(alkylene oxide) groups being present as alkoxy-terminated grafts or blocks linked to the polysiloxane units by silicon-carbon bonds, or as a mixture of these forms and a combination of at least two thereof.

The capsule used in the delivery system according to the invention may be of any desired construction. An example of a suitable construction is a combination of a core and a membrane, wherein the core comprises the pharmaceutical composition and is encased in a membrane. The delivery rate of the pharmaceutical composition may then be controlled either by the core or the membrane alone or by both of them.

The delivery system according to the invention may be an intrauterine system, an intracervical system or an intravaginal system, and it may be manufactured in several different ways. The traditional method, that is, that the body and the capsule are cast or injection moulded and the parts are then assembled manually by pulling the capsule over the body, may be used. It is also possible to use the manufacturing method in which the capsule is pulled over the body and the capsule is further coated with a membrane for example by pulling a thin tube over it, as disclosed for example in the patents U.S. Pat. No. 5,400,804 and U.S. Pat. No. 5,369,943. A further manufacturing process is disclosed in the following.

The invention further concerns one manufacturing process of a delivery system, said system comprising a body construction and at least one capsule containing a pharmaceutical composition, said process being characterized in that said body construction is injection moulded and in that said capsule is injection moulded on the body construction in a further step.

This manufacturing process allows the construction of the delivery system in two steps instead of the three steps of the conventional manufacturing process (formation of the body, formation of the capsule and their assembly either manually or mechanically). Furthermore, the process according to the invention may be fully automated, which further decreases the cost of manufacturing and makes its hygiene more easily controllable.

If the capsule has a core-membrane structure, the delivery system according to the invention may be manufactured in the following way: firstly, the body is formed. Secondly, the core is injection molded on the body and thirdly, the membrane is injection molded on the core. In this manufacturing method the correct positioning of the core on the body and the stability of it on the body during the subsequent injection molding of the membrane is of utmost importance and would be difficult to reach without the present invention.

In this manufacturing process, the capsule is preferably symmetrical with respect to its axis that is essentially the same as the axis of the body construction. A symmetrical construction does not affect the flowing of the material during the injection molding, thus allowing the manufacturing of a capsule that is essentially free of internal stresses.

The other embodiments of the invention, namely the ones wherein the body consists of two or more body parts (three, four or five, typically), may be manufactured according to the traditional method or according to the present, inventive method. The body parts may be cast or moulded in a first step, the capsule in a second step, a third step consisting of assembling the parts. An advantage of these constructions is that it is not necessary to pull the capsule over the body, but it is possible to assemble the capsule and a first body part and in a subsequent step, to attach the second body part to the first body part or to the capsule. Different embodiments of the invention are disclosed in the drawings and for a skilled person, it will be apparent from the drawings and their explanations, how to manufacture and assemble the system according to the invention.

The two (or more) body parts may be attached to each other for example by mechanical joints (such as hooks or a pin and hole-structure), by snap joints, by biocompatible adhesive or by resistance wire welding. It is of course evident for a person skilled in the art that any other attaching means and methods may be used.

In this specification, except where the context requires otherwise, the words "comprise", "comprises" and "comprising" means "include", "includes" and "including", respectively. That is, when the invention is described or defined as comprising specified features, various embodiments of the same invention may also include additional features. Also, the reference numerals should not be construed as limiting the claims.

The invention is described below in greater detail by the following, non-limiting drawings.

BRIEF DESCRIPTION OF THE DRAWINGS

FIG. 4 illustrates a part of a body of a delivery system according to a third embodiment of the invention.

FIG. 5 illustrates a part of a body of a delivery system according to a fourth embodiment of the invention.

FIG. 6 illustrates a part of a delivery system according to a fifth embodiment of the invention.

FIG. 7 illustrates a part of a delivery system according to a sixth embodiment of the invention.

FIG. 8 illustrates a part of a delivery system according to a seventh embodiment of the invention.

FIG. 9 illustrates a part of a delivery system according to an eight embodiment of the invention.

FIG. 10 illustrates a part of a delivery system according to a ninth embodiment of the invention.

FIG. 11 illustrates a part of a delivery system according to a tenth embodiment of the invention.

FIG. 12 illustrates a delivery system according to an eleventh embodiment of the invention.

FIG. 13 illustrates a delivery system according to a twelfth embodiment of the invention.

FIG. 14 illustrates a delivery system according to a thirteenth embodiment of the invention.

FIG. 15 illustrates a delivery system according to a fourteenth embodiment of the invention.

DETAILED DESCRIPTION OF THE DRAWINGS

Figure 1A:
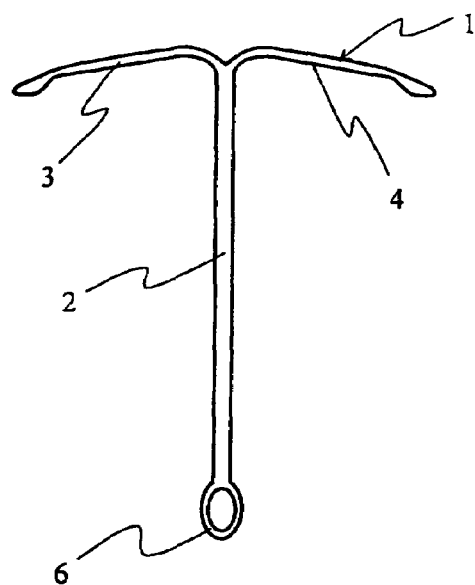
FIG. 1a illustrates a body of a delivery system according to the prior art.
Figure 1B:
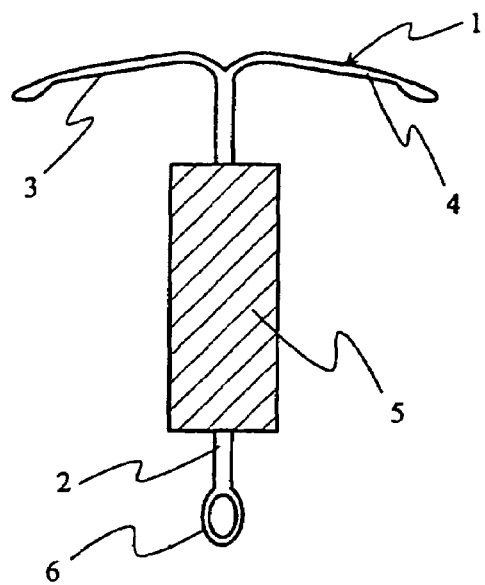
FIG. 1b illustrates a delivery system according to the prior art.

FIGS. 1a and 1b illustrate a body of a delivery system and a delivery system according to the prior art. FIG. 1a shows the body 1 of a known T-shaped intrauterine system. The body 1 consists of an elongate member 2 having at one end a transverse member comprising two wings 3 and 4, the elongate member and the transverse member forming a substantially T-shaped piece when the system is positioned in the uterus. The body 1 is commonly made of a plastic material, for example polyethene, and consists of one piece.

FIG. 1b illustrates a delivery system according to the prior art, comprising a body 1 and a capsule 5 containing a pharmaceutical composition. Said capsule 5 containing a pharmaceutical composition (hereinafter called "the capsule") is commonly a piece made of an elastomeric material, comprising a pharmaceutical composition. The capsule has, along its vertical axis, a canal wherein the elongate member fits. The capsule is positioned on the body by enlarging said canal and then by pulling the capsule over the end 6 of the body. As can be seen from the Figure, there are discontinuities in the outer surface shape of the system.

Figure 2:
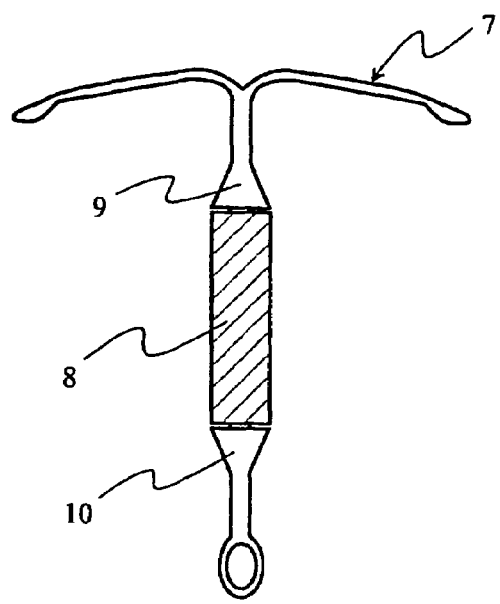
FIG. 2 illustrates a delivery system according to a first embodiment of the invention.

FIG. 2 illustrates a delivery system according to a first embodiment of the invention. The system comprises a body 7 and a capsule 8. The body 7 has two locking parts 9 and 10. Said locking parts are an enlargement of the body. 7 is such a manner that once the capsule 8 is in its final position, there are no discontinuities in the outer shape of the elongate member. The delivery system according to FIG. 2 is preferably an intrauterine system.

In FIG. 2, the construction of the body 7 is not specified. Some examples of said construction are given in FIGS. 3 to 8. In said Figures, the locking parts 9 and 10 both have a first end being in contact with the part of the body that is not in contact with the capsule, once the delivery system is in its final position in the body, and a second end opposite to this first end, said second end facing the capsule(s).

Figure 3:
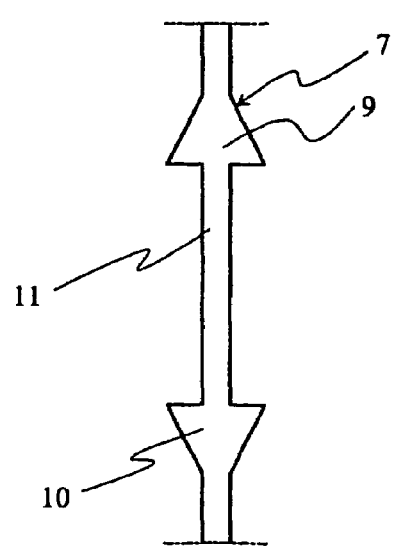
FIG. 3 illustrates a part of a body of a delivery system according to a second embodiment of the invention.
Figure 16:
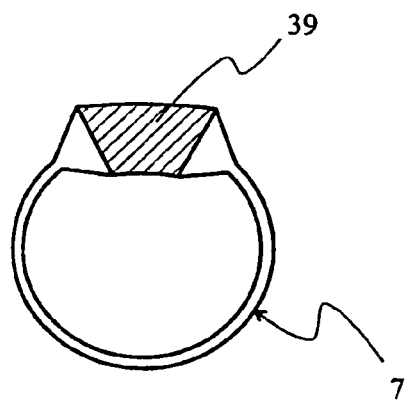
FIG. 16 illustrates a delivery system according to a fifteenth embodiment of the invention.
Figure 17:
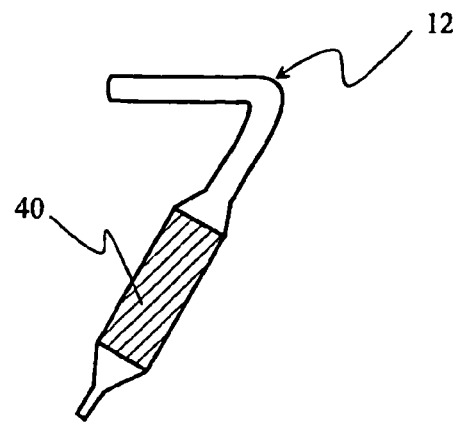
FIG. 17 illustrates a delivery system according to a sixteenth embodiment of the invention.
Figure 18:
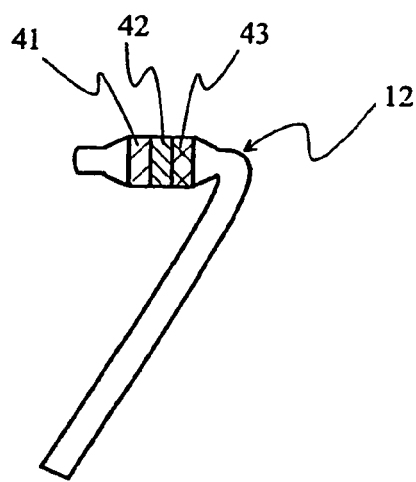
FIG. 18 illustrates a delivery system according to a seventeenth embodiment of the invention.

FIG. 3 illustrates a part of a body of a delivery system according to a second embodiment of the invention. In this embodiment, the body 7 of the delivery system consists of one part wherein the second end of the first locking part 9 continues as a rod 11, said rod continuing as the second locking part 10 at its other end. The body is produced for example by injection moulding as one piece. It is obvious to one skilled in the art that the cross-sectional profile of the rod 11 can be any desired form, such as a circle, a square, a triangle or a polygon. The rod 11 may naturally also have for example the shape of a cone, truncated or not.

FIG. 4 illustrates a part of a body of a delivery system according to a third embodiment of the invention. In this embodiment, the body 12 consists of two parts, the first part comprising the first locking part 9 and the second part comprising the second locking part 10. The first part further comprises, at the second end of the locking part 9, an elongation 13 in the form of a rod with a hook 15 at its end. The second part of the body 12 further comprises, at the second end of the locking part 10, an elongation 14 in the form of a rod with a hook 16, identical but mirror image of the hook of the elongation 13, at its end. Said elongations 13 and 14 are constructed in such a manner that once the capsule is placed over one of the elongations, the other elongation is passed inside the capsule and the hooks are connected so as to form a continuous rod.

FIG. 5 illustrates a part of a body of a delivery system according to a fourth embodiment of the invention. This embodiment comprises also a body 12 consisting of two parts, in a similar manner to the embodiment shown in FIG. 4. The difference to the third embodiment is that instead of the hooks, the elongation 13 comprises a pin 17 whereas the elongation 14 comprises a hole 18 which diameter is essentially identical to the outer diameter of the pin 17.

FIG. 6 illustrates a part of a delivery system according to a fifth embodiment of the invention. In this embodiment, the body 12 consists of two parts as in the third and fourth embodiments, but here the junction of the two parts is made with an adhesive. The Figure shows the body 12 and a part of the capsule 8 as well as the junction 19 consisting of an adhesive. It is obvious to one skilled in the art that it is possible to use any biocompatible adhesive. It is also possible to use for example resistance wire welding.

FIG. 7 illustrates a part of a delivery system according to a sixth embodiment of the invention. The FIG. 7 shows the body 12 consisting of two parts and the capsule 8. The second ends of the locking parts 9 and 10 comprise elongations 20 and 21 in the form of an arrow. The ends of the capsule 8 comprise cavities that are essentially of the same form and size as the arrows of the elongations 20 and 21. The capsule 8 is thus attached between the locking parts with snap joints.

FIG. 8 illustrates a part of a delivery system according to a seventh embodiment of the invention. This embodiment is similar to the sixth embodiment, the difference being that the cavities are within the locking parts 9 and 10, and the elongations within the capsule 8. In this embodiment, it is also shown that the diameter of the cross-section of the capsule 8 is not necessarily constant over the length of the capsule.

FIG. 9 illustrates a part of a delivery system according to an eighth embodiment of the invention. In this embodiment, the surfaces of the ends of the capsule 8 are smaller than the surfaces of the locking parts 9 and 10.

FIG. 10 illustrates a part of a delivery system according to a ninth embodiment of the invention. In this embodiment, the locking parts 22 and 23 have a rounded shape and the cross-sectional diameter of the capsule 24 is not constant over the length of the capsule.

FIG. 11 illustrates a part of a delivery system according to a tenth embodiment of the invention. The system according to this embodiment comprises three capsules 29, 30 and 31 that are separated from each other by locking parts 25, 26, 27 and 28. In this embodiment, the diameter of the locking parts varies along their length for the locking parts 25 and 28 but not for the locking parts 26 and 27.

FIGS. 12 to 22 illustrate different forms of the intrauterine system and of the capsule containing a pharmaceutical composition.

FIG. 12 illustrates a delivery system according to an eleventh embodiment of the invention. The Figure shows the capsule 32 having three ends and the body 12 consisting of two parts.

FIG. 13 illustrates a delivery system according to a twelfth embodiment of the invention, showing the capsule 33 in the form of an "L" and the body 34 consisting of three parts.

FIGS. 14 and 15 illustrate a delivery system according to a thirteenth and a fourteenth embodiment of the invention. In the thirteenth embodiment, the T-shaped body 7 comprises one capsule 36 in one of the wings of the body. In the fourteenth embodiment, the T-shaped body 7 comprises in addition a second and a third capsule 37 and 38 in the other wing of the body.

Figure 19:
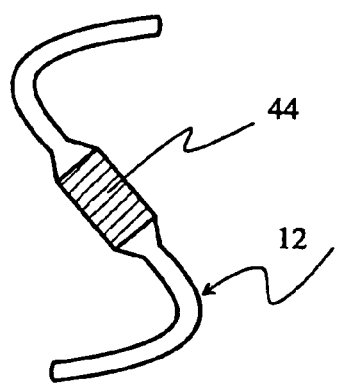
FIG. 19 illustrates a delivery system according to an eighteenth embodiment of the invention.
Figure 20:
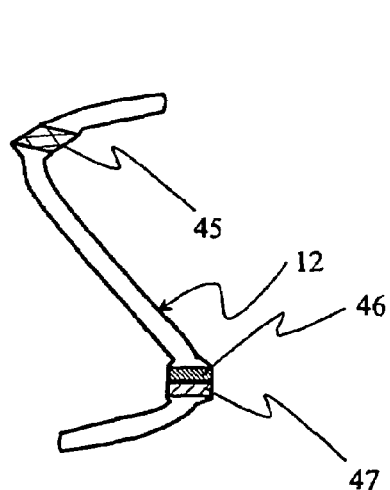
FIG. 20 illustrates a delivery system according to a nineteenth embodiment of the invention.
Figure 21:
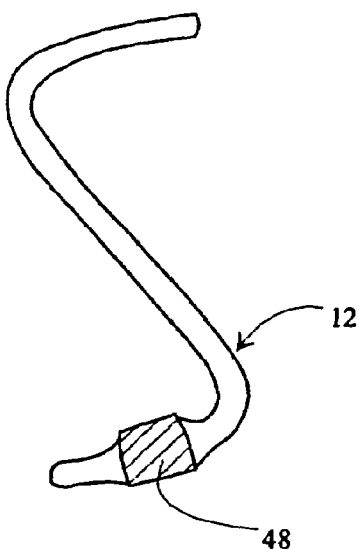
FIG. 21 illustrates a delivery system according to a twentieth embodiment of the invention.
Figure 22:
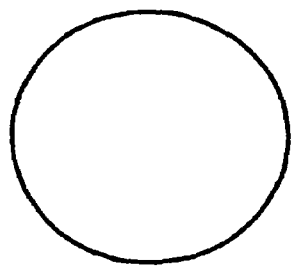
FIG. 22 illustrates a cross-sectional profile of a capsule containing a pharmaceutical composition according to a twenty-first embodiment of the invention.
Figure 23:
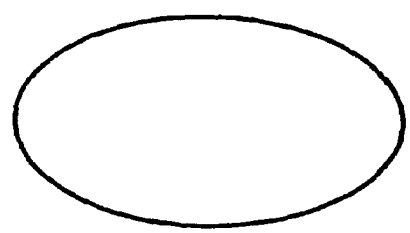
FIG. 23 illustrates a cross-sectional profile of a capsule containing a pharmaceutical composition according to a twenty-second embodiment of the invention.
Figure 24:
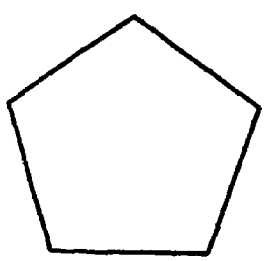
FIG. 24 illustrates a cross-sectional profile of a capsule containing a pharmaceutical composition according to a twenty-third embodiment of the invention.
Figure 25:
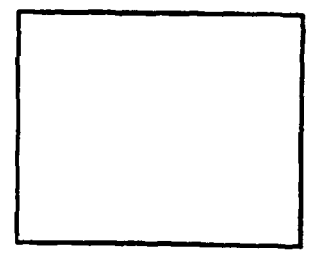
FIG. 25 illustrates a cross-sectional profile of a capsule containing a pharmaceutical composition according to a twenty-fourth embodiment of the invention.
Figure 26:
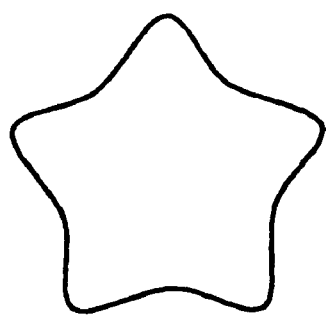
FIG. 26 illustrates a cross-sectional profile of a capsule containing a pharmaceutical composition according to a twenty-fifth embodiment of the invention.
Figure 27:
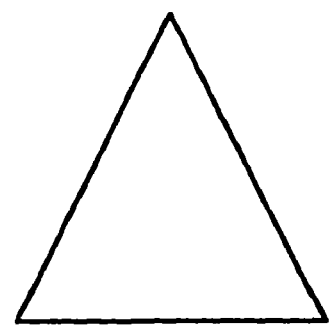
FIG. 27 illustrates a cross-sectional profile of a capsule containing a pharmaceutical composition according to a twenty-sixth embodiment of the invention.
Figure 28:
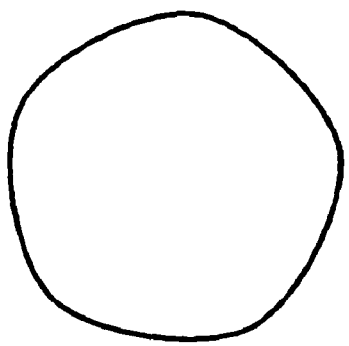
FIG. 28 illustrates a cross-sectional profile of a capsule containing a pharmaceutical composition according to a twenty-seventh embodiment of the invention.
Figure 29:
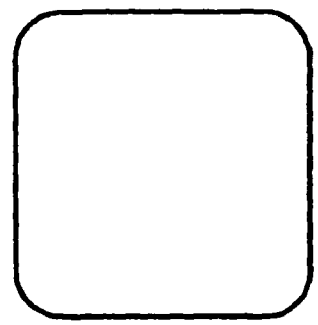
FIG. 29 illustrates a cross-sectional profile of a capsule containing a pharmaceutical composition according to a twenty-eigth embodiment of the invention.
Figure 30:
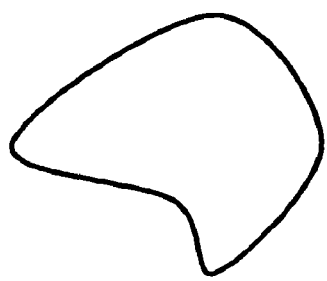
FIG. 30 illustrates a cross-sectional profile of a capsule containing a pharmaceutical composition according to a twenty-ninth embodiment of the invention.

FIGS. 16 to 21 illustrate delivery systems according to the fifteenth to twentieth embodiments of the invention. The fifteenth embodiment of the invention illustrated in FIG. 16 consists of the body 7 in a curved shape so that once the capsule 39 is in place the system has essentially the form of a circle. The body of the sixteenth and seventeenth embodiments is "7-shaped" and in the sixteenth embodiment illustrated in FIG. 17, the system comprises one capsule 40 in the long part of the body. In the seventeenth embodiment illustrated in FIG. 18, the system comprises three capsules 41, 42 and 43 in the short part of the body. FIGS. 19, 20 and 21 illustrate the eighteenth, nineteenth and twentieth embodiments of the invention wherein the body is "S-shaped". In the embodiment illustrated in FIG. 19, the system comprises one capsule 44 and in the embodiment illustrated in FIG. 20, the system comprises three capsules 45, 46 and 47 of which one is placed at a different place than the two other capsules. In the embodiment shown in FIG. 21, the system comprises one capsule 48 near the end of the system.

FIGS. 22 to 30 illustrate cross-sectional profiles of a capsule containing a pharmaceutical composition according to the twenty-first to twenty-ninth embodiments of the invention. The cross-sectional profile may thus be a circle, an ellipse, a polygon (pentagon, hexagon, heptagon, octagon etc.), a rectangle, a triangle, a square or a combination of regular or irregular forms. When regular forms such as rectangles or triangles are used, the corners may be rounded or not. The cross-sectional profile may also have any arbitrary form. It is evident to a person skilled in the art that the forms given in FIGS. 22 to 30 are non-limiting examples.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

The invention claimed is:

1. A delivery system comprising a body construction and at least one capsule containing a pharmaceutical composition, said capsule having at least a first end and a second end, wherein the body construction has at least two locking parts, each locking part having at least a first end and a second end, said first end of each locking part having a surface adapted to face and cover one of the at least first and second ends of the capsule, the diameter of at least one of the locking parts varying along its length between said first end and said second end, and wherein the capsule is mounted between said at least two locking parts, and wherein said locking parts have the shape of a truncated cone, wherein said capsule containing a pharmaceutical composition consists essentially of a biocompatible polymer and at least one pharmaceutically active agent.

2. The system of claim 1, wherein the cross-sectional profile of said at least first or second end of the capsule is essentially identical in size and shape to said surface of the locking part facing said end of the capsule.

3. The system of claim 1, wherein said body construction consists of one body part.

4. The system of claim 1, wherein said body construction consists of at least two body parts.

5. The system of claim 1, wherein the end of the truncated cone having a larger diameter is the end having the said surface facing said end of the capsule.

6. The system of claim 1, wherein the surface of the cross-section of said at least first or second end of the capsule is essentially smaller than said surface of the locking part facing said end.

7. The system of claim 1, wherein it has two or more capsules containing a pharmaceutical composition.

8. The system of claim 1, wherein said system is an intrauterine system.

9. A manufacturing process for a delivery system, said system comprising a body construction and at least one capsule containing a pharmaceutical composition, comprising
    injection molding said body construction, and then
    injection molding said capsule onto said construction body in a separate step, wherein said capsule has at least a first end and a second end, wherein the body construction has at least two locking parts, each locking part having at least a first end and a second end, said first end of each locking part having a surface adapted to face and cover one of the at least first and second ends of the capsule, the diameter of at least one of the locking parts varying along its length between said first end and said second end, wherein the capsule is mounted between said at least two locking parts, and wherein said locking parts have the shape of a truncated cone, wherein said capsule containing a pharmaceutical composition consists essentially of a biocompatible polymer and at least one pharmaceutically active agent.

10. The process of claim 9, wherein said body construction consists of one body part.

* * * * *